US010195076B2

(12) United States Patent
Fateh (10) Patent No.: US 10,195,076 B2
(45) Date of Patent: Feb. 5, 2019

(54) HEAD-MOUNTED DEVICE PROVIDING DIAGNOSIS AND TREATMENT AND MULTISENSORY EXPERIENCE

(71) Applicant: Eye Labs, LLC, Mountain View, CA (US)

(72) Inventor: Sina Fateh, Mountain View, CA (US)

(73) Assignee: EYE LABS, LLC, Mountain View, CA (US)

( * ) Notice: Subject to any disclaimer, the term of this patent is extended or adjusted under 35 U.S.C. 154(b) by 311 days.

(21) Appl. No.: 14/924,590

(22) Filed: Oct. 27, 2015

(65) Prior Publication Data

US 2017/0112666 A1    Apr. 27, 2017

Related U.S. Application Data

(60) Provisional application No. 62/245,871, filed on Oct. 23, 2015.

(51) Int. Cl.
*G02C 7/00* (2006.01)
*G02B 27/00* (2006.01)
(Continued)

(52) U.S. Cl.
CPC .......... *A61F 9/0026* (2013.01); *A61B 3/0083* (2013.01); *A62B 18/00* (2013.01);
(Continued)

(58) Field of Classification Search
CPC ... A61B 5/0015–5/0024; A61B 5/6803; A61B 5/6813; A61B 5/74–5/7445;
(Continued)

(56) References Cited

U.S. PATENT DOCUMENTS 5,171,306 A    12/1992  Vo
5,368,582 A    11/1994  Bertera
(Continued)

FOREIGN PATENT DOCUMENTS

EP    2667237 A1    11/2013

OTHER PUBLICATIONS

U.S. Appl. No. 15/090,863 by Fateh, S., filed Apr. 5, 2016.
(Continued)

*Primary Examiner* — Susan Su
(74) *Attorney, Agent, or Firm* — Perkins Coie LLP (57) ABSTRACT

This application is related to a head-mounted display system and related methods for entertainment, diagnostics, and treatment. The HMD includes various sensors and tools to take physical measurements, perform physical procedures, adjust physical conditions, or manipulate digital data. In some embodiments, the HMD produces different types of sensory stimuli, such as releasing or filtering certain compounds in liquid or aqueous forms in the space near the HMD, or adjusting different physical features of the space near the HMD, such as temperature and flow, to enhance the augmented or virtual reality environment being displayed. In some embodiments, the HMD performs regular monitoring, a specific examination, a surgical intervention, or other care procedures on the eyes automatically or in conjunction with a device of an eye care professional across a computer network to care for the user's eyes in real time or on an ongoing basis.

11 Claims, 10 Drawing Sheets

(51) Int. Cl.
*A61F 9/00* (2006.01)
*G02B 27/01* (2006.01)
*A62B 18/00* (2006.01)
*A61B 3/00* (2006.01)

(52) U.S. Cl.
CPC .... *G02B 27/0172* (2013.01); *G02B 2027/014* (2013.01); *G02B 2027/0138* (2013.01); *G02B 2027/0178* (2013.01)

(58) Field of Classification Search
CPC ............... A61B 5/7455; A61B 5/7465; G02B 27/00–27/01; G06K 9/00–9/00671
See application file for complete search history.

(56) References Cited

U.S. PATENT DOCUMENTS

| | | | |
|---|---|---|---|
| 5,588,564 A | 12/1996 | Hutson et al. | |
| 5,807,357 A * | 9/1998 | Kang | A61M 11/005 604/294 |
| 6,210,000 B1 * | 4/2001 | Yee | A61B 5/411 351/83 |
| 8,128,606 B2 * | 3/2012 | Anderson | A61F 9/0008 600/558 |
| 2010/0163025 A1 | 7/2010 | Hyde et al. | |
| 2011/0041237 A1 | 2/2011 | Gupta et al. | |
| 2011/0160882 A1 | 6/2011 | Gupta et al. | |
| 2012/0127284 A1 | 5/2012 | Bar-Zeev et al. | |
| 2012/0290401 A1 * | 11/2012 | Neven | A61B 3/113 705/14.68 |
| 2014/0098134 A1 * | 4/2014 | Fein | G06T 11/60 345/633 |
| 2014/0198190 A1 * | 7/2014 | Okumu | G02B 27/017 348/53 |
| 2014/0337634 A1 * | 11/2014 | Starner | H04L 9/3231 713/186 |
| 2015/0256564 A1 | 9/2015 | Reynolds | |
| 2016/0015470 A1 * | 1/2016 | Border | G02B 27/017 600/117 |
| 2016/0167672 A1 * | 6/2016 | Krueger | A61M 21/00 340/576 |
| 2016/0259986 A1 * | 9/2016 | Yun | G06K 9/00892 |
| 2016/0270656 A1 * | 9/2016 | Samec | A61B 3/085 |
| 2017/0072283 A1 * | 3/2017 | Davisson | A61B 5/6895 |
| 2017/0117005 A1 * | 4/2017 | Jerauld | G10L 25/63 |
| 2017/0293348 A1 * | 10/2017 | Lee | G08B 7/00 |

OTHER PUBLICATIONS

International Search Report and Written Opinion dated Feb. 2, 2017, of International Application No. PCT/US2016/058208, filed Oct. 21, 2016.
Non-Final Office Action with Restriction Requirement dated Mar. 1, 2017, for U.S. Appl. No. 15/090,863 of Fateh, S. filed Apr. 5, 2016.
U.S. Appl. No. 15/462,341 by Fateh, S., filed Mar. 17, 2017.
U.S. Appl. No. 15/462,375 by Fateh, S., filed Mar. 17, 2017.
U.S. Appl. No. 15/462,445 by Fateh, S., filed Mar. 17, 2017.
Non-Final Office Action dated Nov. 6, 2017 for U.S. Appl. No. 15/090,863 of Fateh, S. filed Apr. 5, 2016.

* cited by examiner

HEAD-MOUNTED DEVICE PROVIDING DIAGNOSIS AND TREATMENT AND MULTISENSORY EXPERIENCE

CROSS-REFERENCE TO RELATED APPLICATIONS

This application claims priority to the U.S. provisional patent application Ser. No. 62/245,871, filed Oct. 23, 2015, which is incorporated herein by reference in its entirety.

TECHNICAL FIELD

The present application is related to a head-mounted device (HMD) of augmented and virtual reality content, and more specifically to methods and systems that improve the effectiveness of an HMD and the comfort of the user.

BACKGROUND

Conventional HMDs can typically be worn by a user like a pair of glasses and enables the user to view augmented or virtual reality content produced by the HMD device instead of the reality.

BRIEF DESCRIPTION OF THE DRAWINGS

Various embodiments are disclosed in the following detailed description and accompanying drawings.

DETAILED DESCRIPTION

This application is related to an HMD system and related methods. Compared with conventional HMD devices, the HMD system disclosed in the present application includes additional components, such as sensors, information capturing devices, illumination devices, operational devices, substance distribution devices, that achieve various entertainment, diagnostics, and treatment purposes for the user's eyes and additional facial areas.

As the HMD system resides in a known position very close to the user's eyes and other facial features, the HMD can readily interact with the user's facial features directly or through changing the environment around those facial features. The HMD can perform various procedures on the eyes with speed and precision.

By providing additional sensory stimuli that simulate the displayed content, the HMD system provides the user with a multisensory entertainment experience in gaming, movie watching, or other similar activities. Furthermore, by monitoring the adjusting the various conditions of the surroundings or the user's eyes or face, the HMD also assures the user of a comfortable environment for enjoying the experience in terms of temperature, humidity, cleanliness, and other factors.

By incorporating various instruments and devices and enabling the user to communicate with care professionals through the wealth of data captured or generated by the HMD system, the HMD eliminates the need for the user to visit the care professionals in their offices and allows the user to receive care instructions and treatments in real time.

References will be made below in the Detailed Description to various embodiments, which are illustrated in the accompanying drawings. The same or similar reference numerals have been used throughout the drawings to refer to the same or like parts. The accompanying figures are included to provide a further understanding of the invention. It will be understood by one skilled in the art that various features of the embodiments described within the Detailed Description and the figures can be used in any and all combinations.

Basic Structure

Figure 1:
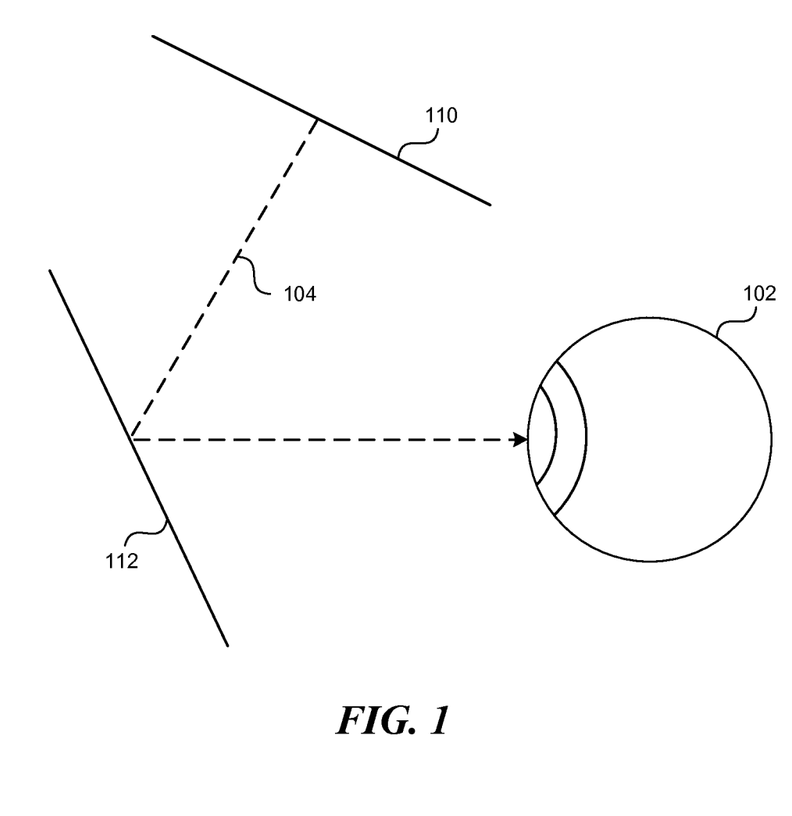
FIG. 1 is a schematic diagram showing basic components of head-mounted device (HMD).

FIG. 1 shows the basic element of an HMD—glasses. Glasses include an image display system 110 and an optical display surface 112 configured to reflect light 104 towards the eye of a user 102. Light 104 can be emitted from the image display system 110 and reflected by optical display surface 112 towards the user's eye 102.

HMDs can display two types of digital imagery. First, some HMDs may be configured to display simulated (e.g., computer-generated) images of a virtual environment. These HMDs are referred to as "virtual reality". Virtual reality is generally achieved by the wearing of a helmet, goggles, etc. that form an enclosed area around the user's eyes. Second, some HMDs may be configured to display simulated (e.g., computer-generated) images that are integrated into real world content perceived by the user. These HMDs are referred to as "augmented reality". Augmented reality allows the user to interact with virtual content in the real world and, in general, distinguish between the two. For example, augmentation may take place through superposition of a simulated image on a non-simulated, real world image, which can allow the user to view additional data relevant to a desired task, the local environment, etc. In various embodiments, the simulated image can be adapted to allow for user interaction.

HMD systems fall into three general categories: binocular, bi-ocular, and monocular. Binocular HMD systems present a separate image to each eye of the user, while bi-ocular HMD systems present a single image to both of the user's eyes, and monocular HMD systems present a single image to only one eye of the user. See, for example, FIGS. 2A and 2B, which demonstrate a binocular HMD system and a monocular HMD system, respectively.

Because binocular HMD systems present two distinct images, the user's eyes must make a constant fusional effort to maintain a simultaneous view of the content. The constant fusional effort required by binocular HMD systems causes eye fatigue and strain, one of the main causes of visual discomfort for users of augmented and virtual reality systems. Those users with weak binocular vision or preexisting visual disorders are more likely to experience severe symptoms and aggravation of their visual disorder.

One of the major challenges of augmented reality is correctly superimposing digital content onto the 3D real world environment perceived by the user. Effective and efficient superposition is complicated due to the difficulty of tracking the user's eyes, which constantly change their fixation distance on various objects.

Figure 2A:
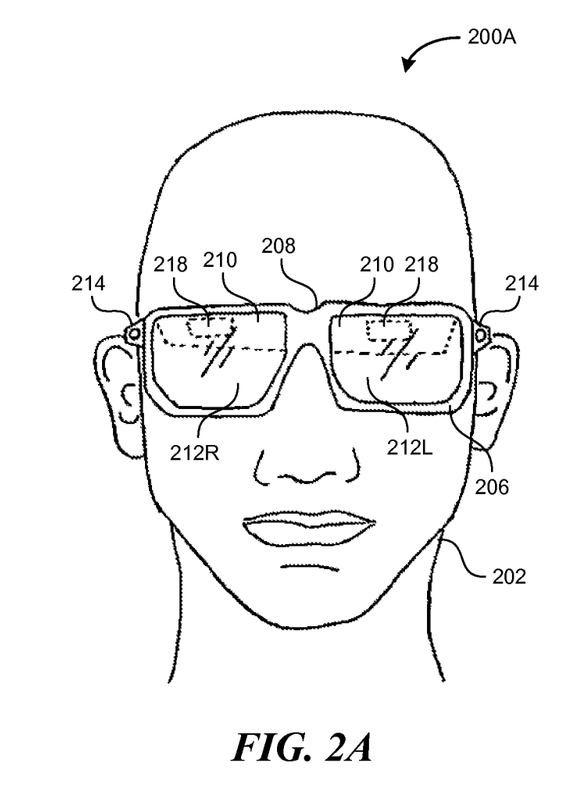
FIG. 2A is a front view representation of an HMD binocular system according to various embodiments.

FIG. 2A is a front view representation of an HMD binocular system 200A according to various embodiments. The HMD binocular system 200A comprises a frame 206, a bridge 208, an image display system 210, an optical display surface 212, and one or more sensors 214. The frame 206 can be configured to support the HMD binocular system 200A similar to conventional glasses. That is, the frame 206 may be configured to be supported by the user's ears and the bridge 208 may be supported by the user's nose. While the HMD binocular system 200A of FIG. 2A resembles conventional glasses, the HMD binocular system 200A may be configured to resemble goggles, a helmet, a visor, etc. The frame 206 of the HMD binocular system 200A can be modified so long as the user 202 can view virtual or augmented reality content on the optical display surfaces 212L, 212R (collectively referred to as "optical display surface 212") in the proper orientation.

The HMD binocular system 200A includes at least one image display system 210 and at least one optical display surface 212. The optical display surface may comprise an optical display surface for the user's left eye 212L and/or an optical display surface for the user's right eye 212R. In various embodiments, the optical display surface 212 may be curved in order to enlarge the viewing field and improve the viewing experience of the user. In some embodiments, the optical display surface 212 may be opaque, thereby allowing the user 202 to view virtual reality content. In some embodiments, the optical display surface 212 may be transparent or semi-transparent, thereby allowing the user 202 to view augmented reality and real world content simultaneously.

The optical display surface 212 may completely surround one or both eyes of the user. As described above, in some embodiments the optical display surface can comprise two separate optical display surfaces (e.g., 212L and 212R). The user's right eye may be shown a first representation of a 3D digital image on optical display surface 212R, and the user's left eye may be shown a second representation of the 3D digital image on optical display surface 212L. The separate optical display surfaces 212L, 212R can be optimized to present the digital environment relative to the location of the user's eyes. The separate optical display surfaces 212L, 212R may be optimized independently or collectively. In some embodiments, the optical display surface 212 can comprise a single optical display surface, some portion of which may be viewed by both eyes and some portion of which may be viewed by only one eye. The bridge 208 may have one or more reflectors arranged adjacent to the optical display surface(s) 212 in order to provide an immersive and realistic digital environment (e.g., virtual reality, augmented reality).

The HMD binocular system 200A can include an electronics module 218, which can process digital virtual and/or augmented reality content, analyze data collected by one or more sensors, optimize digital content presented to the user, etc. The electronics module 218 and HMD binocular system 200A can be powered through a wired or wireless (e.g., battery) medium.

One or more image display systems 210 can be mounted inside the optical display surface 212 or just outside of the optical display surface 212. For example, a first image display system may be configured to display on optical display surface 212L, and a second image display system may be configured to display on optical display surface 212R. The image display system 210 can display the same digital image, similar digital images, or distinct digital images to the user 202. The placement of the image display system 210 may relate to the placement and angle of the optical display surface 212.

Moreover, the placement and angle of image display system 210 may depend on one or more properties (e.g., pixel count, resolution, brightness) of the digital content that is to be projected onto, and reflected from, the optical display surface 212. The image display system 210 may, for example, use light emitting diodes (LEDs), liquid crystal displays (LCDs), organic light emitting diodes (OLEDs), or some combination thereof. In general, the image display system 210 uses small-form displays capable of high resolution (i.e., high pixel density) display, which can provide a more realistic virtual reality environment for the user 202.

A sensor 214 may be coupled to the frame 206 and/or the optical display surface 212 to monitor various aspects of the user's local real world environment. The sensor may, for example, be coupled to opposite sides of the HMD binocular system 200A and configured to gather data, which can be processed and analyzed by the electronics module 218. The data gathered by the sensor 214 may be used by the electronics module 218 to optimize digital content presented to the user 202. The sensor 214 may be coupled to the electronics module 218 to receive power. Alternatively, the sensor 218 may be configured to receive power from a distinct power source. Sensor 214 may be a camera configured to capture the user's interactions with the local environment, a light sensor configured to track illuminance levels within the local environment, an audio sensor configured to sense vocal commands, etc. In some embodiments, a plurality of sensors 214 may be coupled to the frame 208. The plurality of sensors 214 may be a plurality of the same sensor (e.g., more than one camera) or a combination of various sensors, such as those described above. The plurality of sensors 214 can be chosen such that a particular HMD system can be adapted for particular applications (e.g., outdoor use, athletic activities).

Figure 2B:
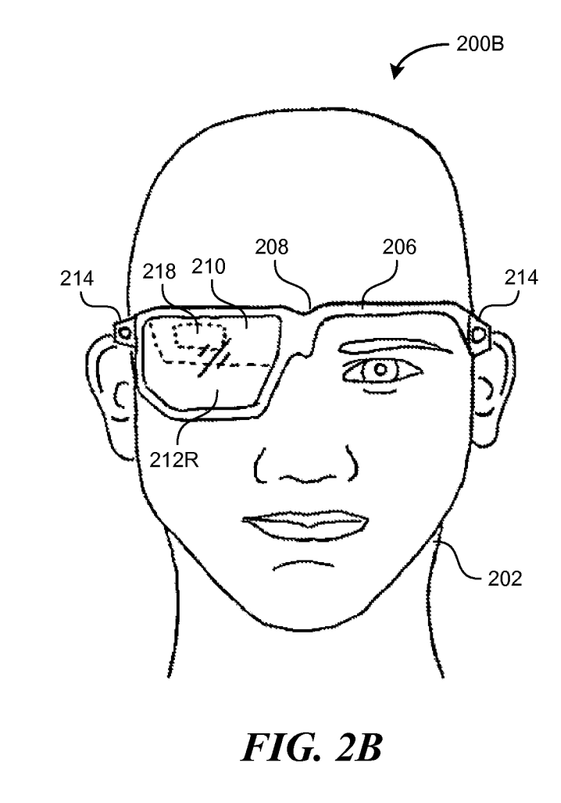
FIG. 2B is a front view representation of an HMD monocular system according to various embodiments.

FIG. 2B is a front view representation of an HMD monocular system 200B according to various embodiments described herein. The HMD monocular system 200B comprises a frame 206, a bridge 208, an image display system 210, an optical display surface 212R, and one or more sensors 214. HMD monocular system 200B is, in large part, comparable to HMD binocular system 200A described above. One skilled in the art will recognize the similarities and, accordingly, only the differences will be discussed.

HMD monocular system 200B comprises an image display system 210 and an optical display surface 212R. In contrast to HMD binocular system 200A, HMD monocular system 200B may only have a single image display system 210 and optical display surface 212. See, for example, FIG. 2B, which illustrates HMD monocular system 200B as comprising an optical display surface for the user's right eye 212R. However, the optical display surface 212 of HMD monocular system 200B can be adapted for a user's left eye (e.g., optical display surface 212L) or right eye (e.g., optical display surface 212R).

In various embodiments, an HMD binocular system 200A may comprise two distinct monocular optical displays. The HMD binocular system 200A can comprise a first optical display configured to present augmented or virtual reality content up to a predetermined distance away, and a second optical display configured to present augmented or virtual reality content whose distance exceeds the predetermined distance. For example, the HMD binocular system 200A may comprise a first optic display that presents content for long-range viewing (e.g., greater than 1, 2.5, 5 meters) and a second optic display that presents content for close-range viewing (e.g., less than 1, 2.5, 5 meters), thereby creating a combined HMD system. For example, the first optic display may use optical display surface 212L, while the second optic display may use optical display surface 212R.

The combined HMD system may further comprise an electronics module (e.g., electronics module 218) that supports a visual balancing software module. The visual balancing software module may, for example, use a fusional stabilizer system to balance the two distinct images displayed on the first optical display and the second optical display. In some embodiments, the combined HMD system can switch from a binocular viewing mode (i.e., first optical display and second optical display displayed simultaneously) to a monocular viewing mode, whereby one image display system 210, or part of the image display system 210, and its corresponding optical display surface (e.g., 212L) are turned off or put into sleep/hibernate mode. Content can only be displayed to one of the user's eyes when the HMD system is in monocular viewing mode.

In some embodiments, the combined HMD system may use progressive optical lenses for one or both of the user's eyes. Progressive optical lenses are characterized by a gradient of increasing lens power distributed throughout the lens associated with each of the user's eyes. Accordingly, the first optical display and second optical display may be configured to use a similar or distinct gradient depending on the requirements of each of the user's eyes. The progressive optic lenses can be configured to support binocular HMD systems, thereby allowing the user to train both eyes on a single optical focal point.

Figure 3A:
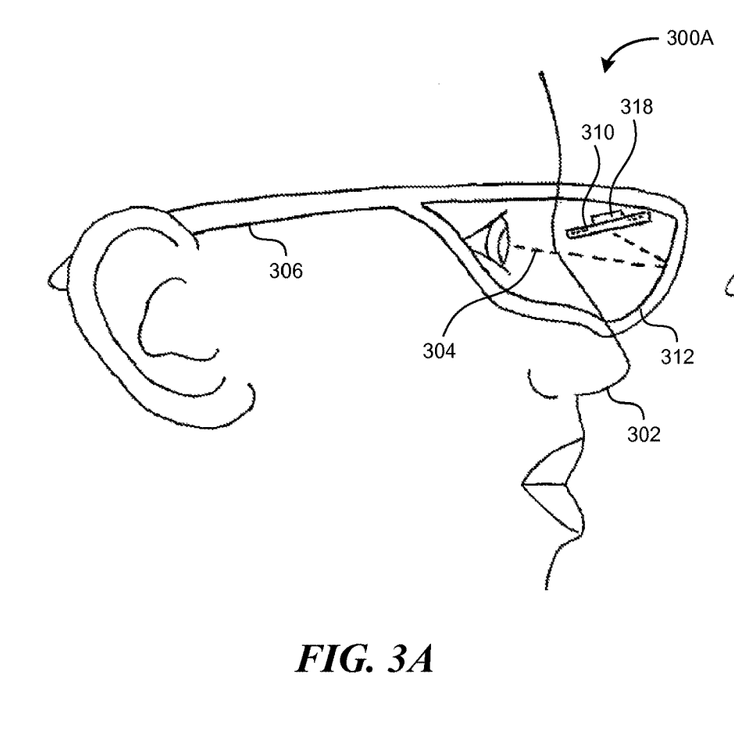
FIGS. 3A and B are side view representations of various HMD systems according to various embodiments.
Figure 3B:
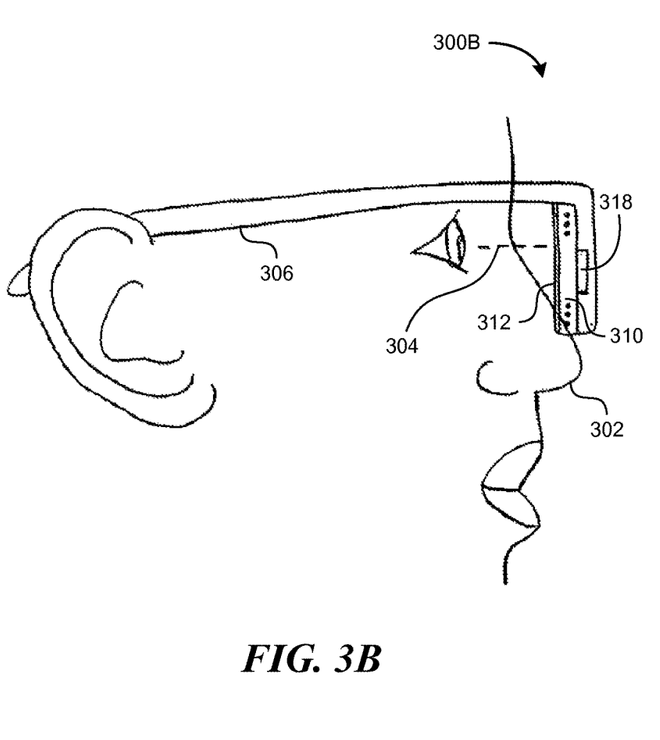

FIGS. 3A and 3B are side view representations of HMD systems (e.g., HMD systems 200A, 200B of FIGS. 2A-B) according to various embodiments. HMD system 300A may comprise a frame 306, an image display system 310, an optical surface display 312, and an electronics module 318. The frame 306, which may be frame 206 of FIG. 2, can be configured to be supported by the user's ears and the bridge may be supported by the user's nose. In some embodiments, the image display system 310 can emit light 304 to be displayed on, and reflected from, an optical display surface 312. Thus, the light 304 (e.g., digital image) is reflected towards a user's eye(s) due to the projection of the image display system 310 towards an angled optical display surface 312. HMD system 300A may comprise a binocular optical display or a monocular optical display as described above. The electronics module 318 can control the digital content projected by the image display system 310.

Similarly, HMD system 300B (e.g., HMD systems 200A, 200B of FIGS. 2A-B) may comprise a frame 306, an image display system 310, an electronics module 318, and, optionally, an optical surface display 312. In some embodiments, the image display system 310 may be configured to emit light 304 directly towards the user's eye. When the light 304 is emitted directly towards the user's eye, the optical display surface 312 may be present in select embodiments. The optical display surface 312 may be included in order to improve effectiveness in certain environments or for certain users, but may not be necessary depending on the arrangement of the image display system 310 and optical display surface 312. The optical display surface 312 may not be required in some embodiments to redirect the light 304 emitted by the image display system 310. As described above, HMD system 300B may comprise a binocular optical display or a monocular optical display. An electronics module 318 can process the digital virtual or augmented reality content projected by the image display system 310 to one or both of the user's eyes.

The image display system 310 of HMD systems 300A, 300B may be configured to project virtual or augmented reality content. In some embodiments, the optical display surface 312 may be opaque, transparent, or semi-transparent depending on the content type, intended viewing environment, etc. For example, the optical display surface 312 may be opaque for virtual reality applications, and transparent or semi-transparent for augmented reality content. In various embodiments, the optical display surface 312 may be selected based on its reflective and/or transmissive properties.

Figure 4:
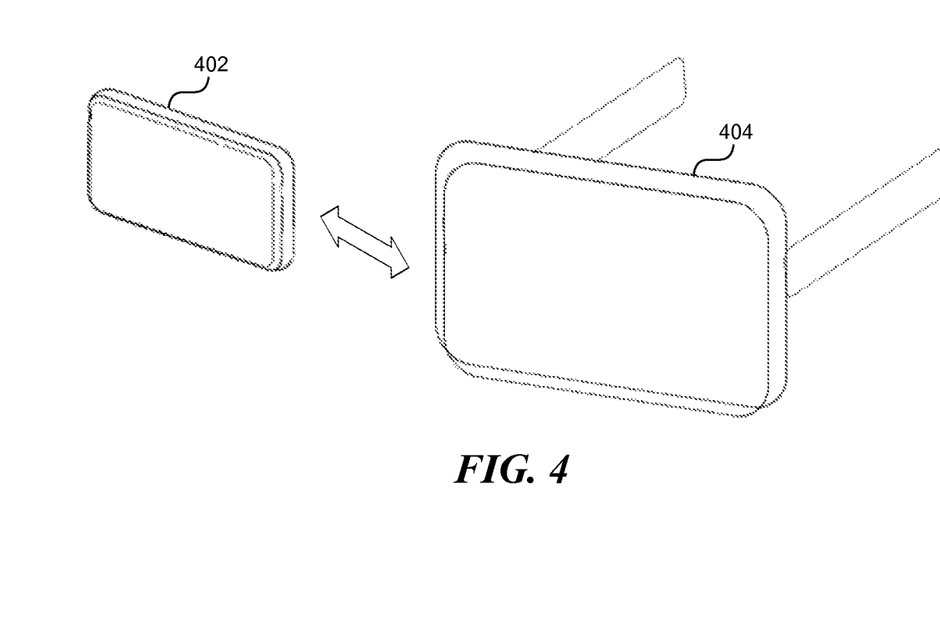
FIG. 4 illustrates example implementations of the display portion, including the optical display surface.

FIG. 4 illustrates example implementations of the display portion of the HMD, including the optical display surface. In some embodiments, the HMD can include a built-in display screen 404. Alternatively, HMD can include an adjustable frame into which an existing mobile device 402, such as a cellular phone, can be inserted.

Additional Features

FIGS. 5A-E illustrate various sensors, instruments, and other components embedded in the HMD for entertainment, diagnostics, and treatment purposes. The sensors could be embedded, installed, or incorporated into the HMD system in the same ways the existing components are integrated or through standard wielding, latching, and similar processes.

Figure 5A:
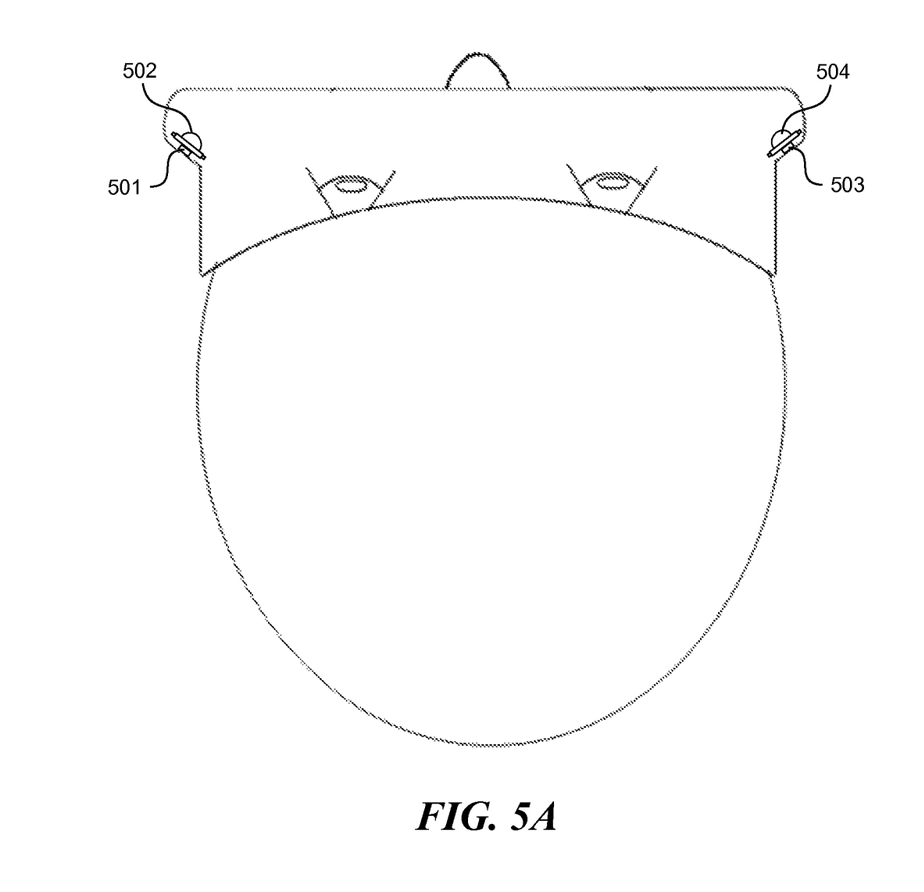
FIGS. 5A-E illustrate various sensors, instruments, and other components embedded in the HMD for entertainment, diagnostics, and treatment purposes.

In some embodiments, as illustrated in FIG. 5A, the HMD system includes a humidifier 502 comprising a reservoir storing water, eye drops, or other appropriate types of liquid and an adjustable dispenser that dispenses the liquid in the reservoir in specific manners. The liquid can be produced in a particular temperature, amount, force, etc. The humidifier can be installed at a docking port 501 on the HMD where liquid distribution is appropriate or desired without obstructing the path between the eyes and the optical display surface. The docking port 501 is coupled to the electronics module 218, from which it receives instructions when to dispense the liquid, and the appropriate amount, frequency, and direction of liquid to dispense. The HMD can also include a dehumidifier for the opposite purpose. The HMD can include additional components, such as an air pumper or regulator 504, that similarly change the air quality, appearance, flow, etc. These instruments can be attached to the HMD at a docking port.

Figure 5B:
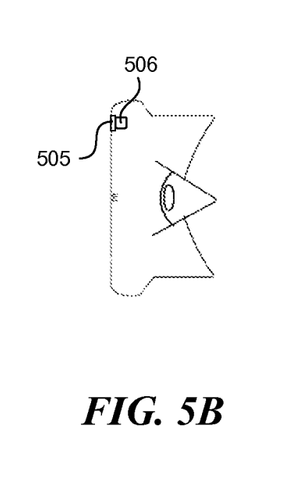

In some embodiments, as illustrated in FIG. 5B, the HMD system includes one or more cameras 506 looking to the eyes of the user. The camera can be installed near the edges of the optical display surface, for example. The HMD also provides a controlled lighting environment. The HMD can incorporate an adjustable light source that emits artificial light at a location that is close enough to the eyes that the light can reach the eyes. The HMD can also control the amount of natural light reaching the eyes by extending the one-dimensional frame in front of the eyes to a compartment, a box, or otherwise enclosed spaces, by including drapes or doors to the one-dimensional frame, and so on.

Figure 5C:
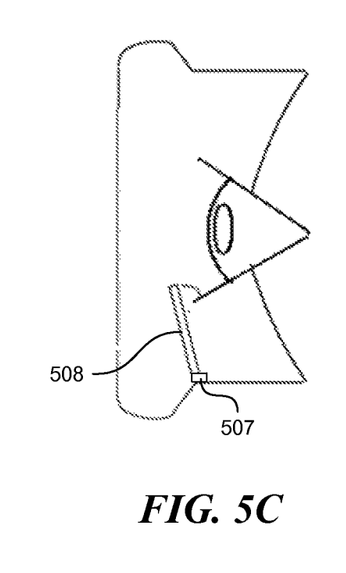
Figure 5D:
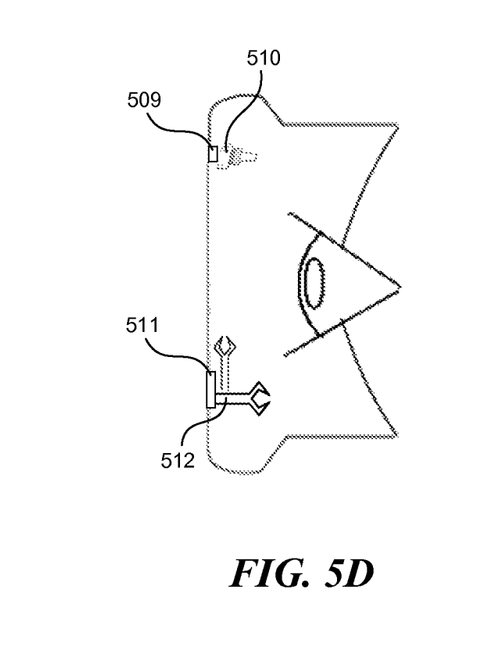
Figure 5E:
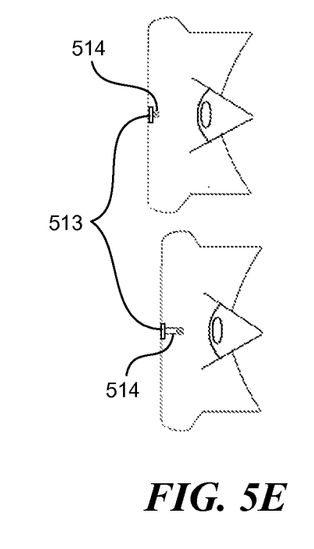

In some embodiments, as illustrated in FIGS. 5C-5E, the HMD system includes one or more components that can perform surgical interventions on the user's eyes. One example component is one or more eyelid speculums 508 near the eyes to hold the eyelids still and keep the eyes open. These speculums can normally be in a contracted configuration and only extend to perform its designed function when instructed or necessary. Another example component is a set of robotic arms 512 that are capable of transporting an object into and out of the eyes. Such an arm can incorporate cutting devices or suturing devices at the one end that is in contact with the eyes. Yet another example component is a medication dispenser 510 that is similar to a humidifier and delivers saline solution, alcohol, medications, and other ingredients into the user's eyes. Yet another example component is an eye pressure sensor 514 that can perform ocular telemetry on the user's eyes. It is to be appreciated that additional components for eye surgery and restoration purposes can be incorporated into the HMD system.

In some embodiments, the HMD system includes a component that changes the fit of the HMD system on the user. For example, the component can change the shape of a portion of the HMD system, such as the bridge or the ear piece of the frame, so that the portion clings more onto the user's face and thus exerts more pressure on the user's face.

Figure 6:
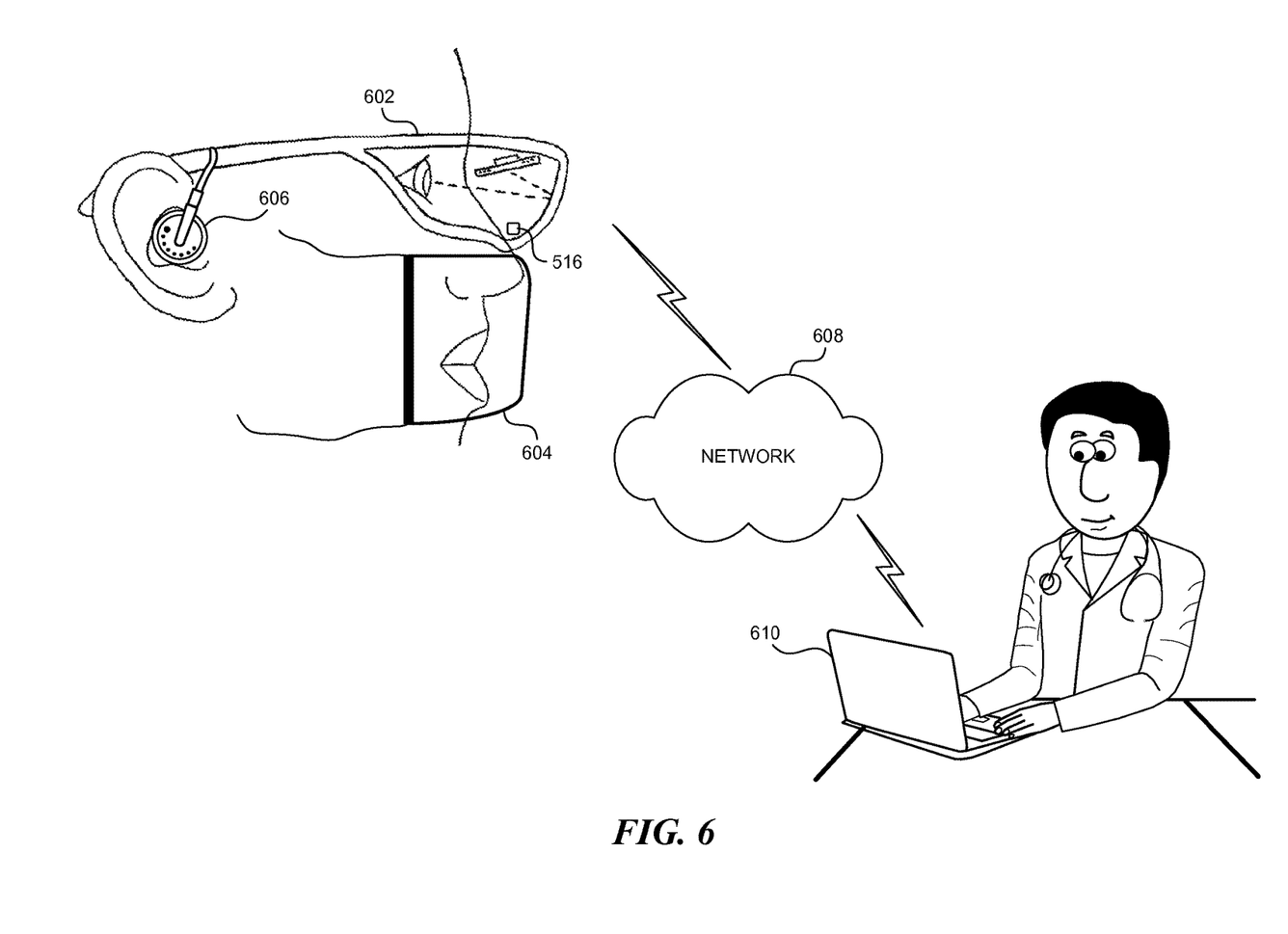
FIG. 6 illustrates additional components that can be integrated with the head-mounted device and the communication path with an external device across a computer network.

FIG. 6 illustrates additional components that can be integrated with the HMD system and the communication path between the HMD system and an external device across a computer network. In some embodiments, the HMD system is integrated with detachable nose or mouth masks 604 (separately or in combination as shown) to cover the user's nose and mouth. Such a mask can include a component similar to the humidifier that produces liquid or steams. The nose mask can also include a component that produces gas or other compounds to regulate or refresh air. Like the glasses, the nose mask or the mouth mask can also include sensors to detect the user's physical condition, such as the color, radiance, elasticity, pressure, dryness, or temperature of the skin or what is underneath the skin. The HMD can work alone or in conjunction with one or both of the nose mask and mouth masks.

In some embodiments, the HMD system incorporates or is integrated with sound equipment. The HMD includes a microphone at closer to the user's mouth as possible to capture the user's sound, which can then be transmitted to a remote source via the HMD's wireless capabilities. The HMD also includes one or more speakers or headphones 606 near the user's ears to transmit sound to the user, which could also originate from a remote source.

In some embodiments, one or more of the additional features of the HMD system are activated or deactivated automatically based on predetermined conditions or manually through controls on the HMD systems, and locally by the user wearing the HMD device or remotely by another device 610 through the computer network 608.

In various embodiments, the plurality of instruments described here, such as 502, 504, 506, 508, 510, 512, 514 are attached to the HMD via the electronic docking ports 501, 503, 505, 507, 509, 511, 513. The electronic docking ports are coupled to the electronics module 218, from which they receive instructions comprising an instrument ID, an action associated with the instrument, and a time associated with the action. For example, when in eye speculum is mounted on the HMD, the HMD registers that an eye speculum is associated with a docking port 507. When conditions are right, the HMD sends an instruction to the eye speculum 508, the instruction comprising an ID associated with the eye speculum, an instruction to expand, and a time at which to expand the eye speculum. Next, the HMD sends an instruction to the eye speculum 508, the instruction comprising an ID associated with the eye speculum, an instruction to retract, and a time at which to retract the eye speculum.

The conditions to send an instruction to an instrument 502, 504, 506, 508, 510, 512, 514, can be determined automatically by the HMD, can be based on downloaded instructions, or can be transmitted over the network 608 based on instructions provided by the healthcare provider device 610. Further details are explained in FIG. 7.

According to one embodiment, the HMD comprises a rail configured to transport the instruments 502, 504, 506, 508, 510, 512, 514 along the rail track, according to an instruction received from the electronics module 218.

For Entertainment

In some embodiments, the HMD system enriches the augmented or virtual reality display with additional sensory stimuli. Depending on the content of the display, the HMD changes the physical environment by changing humidity, light, air flow, temperature, odor, or other conditions in the space affected by the HMD. As one example, when the display includes rain or a fountain, the HMD can spray liquid to simulate the rainfall or the fountain splash. As another example, when the display includes a beach, the HMD can produce a scent from mixing salt and tropical flowers, some breeze, the sound of waves, etc. For realistic simulation of the displayed content, the strength, direction, frequency, and other features of the sensory stimulus would resemble the features of the corresponding item in the display.

In some embodiments, to determine when to produce sensory stimuli in accordance with the displayed content, the HMD can rely on signals provided by the source of the displayed content. For example, the source of a video might send distinct instructions that are embedded in metadata of the video or in separate forms and that indicate when to generate a sensory stimulus and what to generate, to the HMD in real time or in advance. A video itself may also include signals. The HMD can then perform image or video analysis using existing techniques to identify easily-recognizable markers that signal simulation or identify common sensory stimuli or sources thereof, such as rain or tear drops, plants, and animals.

In some embodiments, the user can preset a preferred range for each feature of a sensory stimulus, and the HMD can map the initially produced value for a sensory stimulus into the preferred range. The user can also predetermine what types of sensory stimuli to apply and when to apply them. For example, the user may wish to receive only olfactory stimuli or only sensory stimuli for augmented reality. In addition, the user is allowed to manually adjust different features of the sensory stimuli. The user can make adjustments using spoken words, gestures, physical controls on the HMD, or other mechanisms to generally signify increase or decrease, intensification or weakening, etc.

For Diagnostics and Treatment

In some embodiments, the HMD system allows the user to undergo an eye examination without visiting the doctor's office. The HMD gives recorded visual or audio instructions or real-time instructions. The real-time instructions can be automatically generated or received from a device across a network operated by the person conducting the examination, such as an ophthalmologist, optometrist, or orthoptist. The examiner's device could be any computing device, such as a desktop computer, a laptop computer, a mobile phone, a tablet, or a wearable device. The HMD displays relevant content, such as a real-time video of the examiner, a Snellen chart, or an anatomical view of the portion of the eye being examined. The HMD additionally controls other conditions of the space around the eyes, such as lighting, to facilitate the examination.

In some embodiments, during the examination, the HMD transmits any data produced, such as the user's speech, photos or videos of the user's eyes, various test results of the user's eyes, and the HMD's auto-generated instructions, to the device operated by the examiner in real time. Upon processing these data, such as listening to the user's speech or zooming in or magnifying a portion of a received image, the examiner in turn can adjust the examination procedures based on the data received from the HMD. For example, the examiner can ask the user to close the user's eyes for a few seconds or send a command to the HMD to dispense some eye drops to the user's eyes after seeing a real-time photo of the user's fatigued or dry eyes.

In some embodiments, the HMD can also automatically provide appropriate instructions based on the generated or captured data. For example, in response to an instruction to look to the left, the user may look to the right instead. From the photo or video of the user's eyes, the HMD can determine that the user is looking in the wrong direction using existing image analysis techniques and issue another instruction for the user to look in another direction.

In some embodiments, the HMD system performs surgical interventions on the user's eyes. During a surgery, the HMD administers anesthesia, pain relief, or other medications to the user's eyes. The HMD also operates on the eyes, such as inserting an implant or placing intraocular lenses. The user can also receive surgical tapes, bandages, and similar medical supplies from the HMD.

In some embodiments, the HMD constantly or periodically monitors the conditions of the user's eyes, such as dryness, redness, or pressure, and automatically implements care routines or contact care professionals when the conditions become undesirable with respect to predetermined thresholds. The monitoring can involve non-invasive measures, such as taking photos of the eyes or counting the number of times the eyes have blinked within a given period of time. The HMD can also employ specific embedded tools to test the conditions of the eyes. For example, the HMD can implement the Schirmer's Test or an osmolarity test to detect dry eyes.

In some embodiments, upon detecting undesirable conditions, the HMD performs care procedures to provide relief and comfort to the eyes. As one example, for dry eyes, the HMD can inject eye drops into the user's eyes or generate mists to increase the humidity of the space near the eyes. As another example, for irritated eyes, the HMD can apply a cold compress by splashing water on the user's eyes and face and placing ice cubes on closed eyelids or improve the air quality in the space around the eyes.

In some embodiments, the glasses, the nose mask, or the mouth mask also transmits additional test results obtained by the sensors, such as the blood pressure or skin dryness, to the devices of various nurses or doctors across computer networks. Furthermore, the masks can similarly include additional devices, instruments, and other components for examination and treatment purposes. The HMD therefore also enables the user to work with care professionals regarding health issues even when the user is not physically in front of these care professionals.

Figure 7:
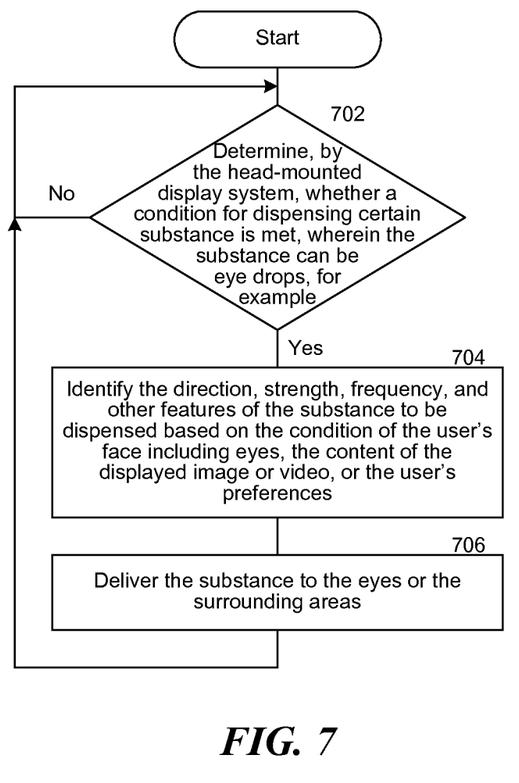
FIG. 7 illustrates a process performed by the HMD system to distribute ingredients to the user's eyes or face or the space near the HMD for the user's comfort, relief, or entertainment.

FIG. 7 illustrates a process performed by the HMD system to distribute ingredients to the user's eyes or face or the space near the HMD for the user's comfort, relief, or entertainment. In step 702, the HMD determines whether a condition for dispensing a certain substance is met. The HMD can also have a similar condition for changing the environment, such as temperature and flow. The condition could be based on the augmented or virtual reality content being displayed, the condition of the user's eyes, the user's preferences (e.g., every hour), and so on. For example, a condition may be that the displayed video includes raindrops or that the dryness of the user's eyes is above a predetermined threshold. When the determination result is positive, in step 704, the HMD determines how to prepare the substance or ingredient for delivery. Specifically, the HMD identifies the final destination, such as the eyes, the strength, potency, or volume of the substance, ranging from a little mist to anesthesia, the frequency, such as every second for five seconds, or other attributes. When the production and distribution of the substance is based on the displayed content, these attributes should match or be consistent with those of the corresponding items in the display. When the production and distribution is based on care instructions, the care instructions can be downloaded onto the electronics module 218, or the care instructions can be received via the network 608 from a device associated with a healthcare provider 610. For example, the instruction can be to distribute 3 antibiotic drops to the eyes at 8 AM, 2 PM, and 8 PM. At each of the specified times, the electronics module 218 sends an instruction to the HMD, the instruction comprising an instrument ID associated with the drop dispenser, and an instruction to deliver 3 drops to the eye. In step 706, the HMD then delivers the prepared substance in the appropriate strength to the final destination in the appropriate frequency. When the determination result is negative, the HMD can re-determine whether the initial condition is met according to a predetermine schedule, for example.

Figure 8:
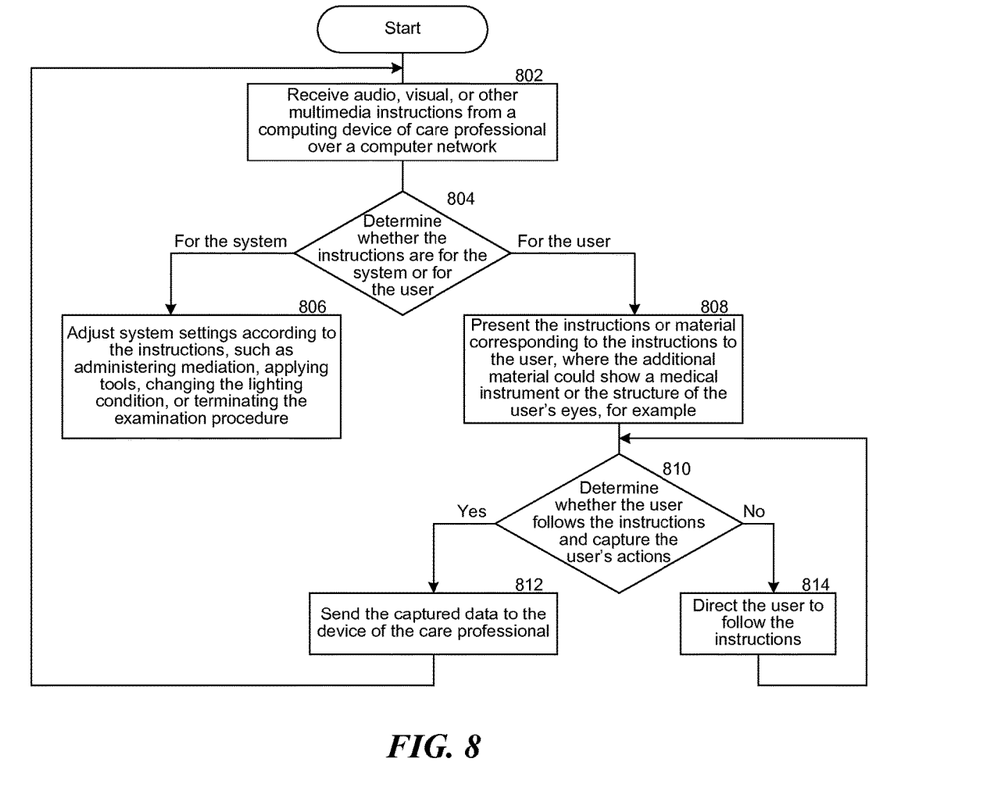
FIG. 8 illustrates an example process performed by the HMD system to perform an eye examination and or surgical intervention.

FIG. 8 illustrates an example process performed by the HMD system to perform an eye examination and/or a surgical intervention. In step 802, the HMD receives instructions from a computing device of a care professional, such as a nurse, a doctor, or a certified practitioner, across a computer network. The computing device can be equipped with a microphone or a camera to record the care professional's actions and capture any other material presented by the care professional. In step 804, the HMD determines whether the instructions are for the HMD or for the user. When the instructions are for the user, in step 808, the HMD presents the instructions to the user, through the display screen, the speaker or headphone, and so on. The HMD can also present relevant material to the user at the same time, such as a Snellen chart or some soothing music. In step 810, the HMD determines whether the user follows the instructions. Step 810 and step 814 can be optionally performed by the HMD to automatically provide clarifications or instruct the user to correct his actions to reduce network traffic and expedite examination. For example, in step 814, the HMD might detect that the user has asked a question and could automatically provide an answer. The HMD might also detect inaction or incorrect action and might restate the instruction in the same or a different form. Furthermore, the HMD captures some or all of the user's actions, including the asking of questions, the commenting on specific issues, and any changes in the user's physical conditions. In step 812, the HMD transmits some or all of the captured data to the computing device of the care professional. What to capture and what to transmit to the care professional can be based on the user's preferences, the HMD's workload, the network traffic, the care professional's preferences, etc. Referring back to step 804, when the instructions are for the HMD, in step 806, the HMD generally follows the instructions. For example, the instructions could be for administering certain solutions or medications or applying certain medical supplies to the user's eyes and surrounding areas; changing the lighting condition; displaying specific visual content or playing specific audio; operating specific instruments to insert an implant to the user's eyes; or halting or terminating the entire procedure.

Figure 9:
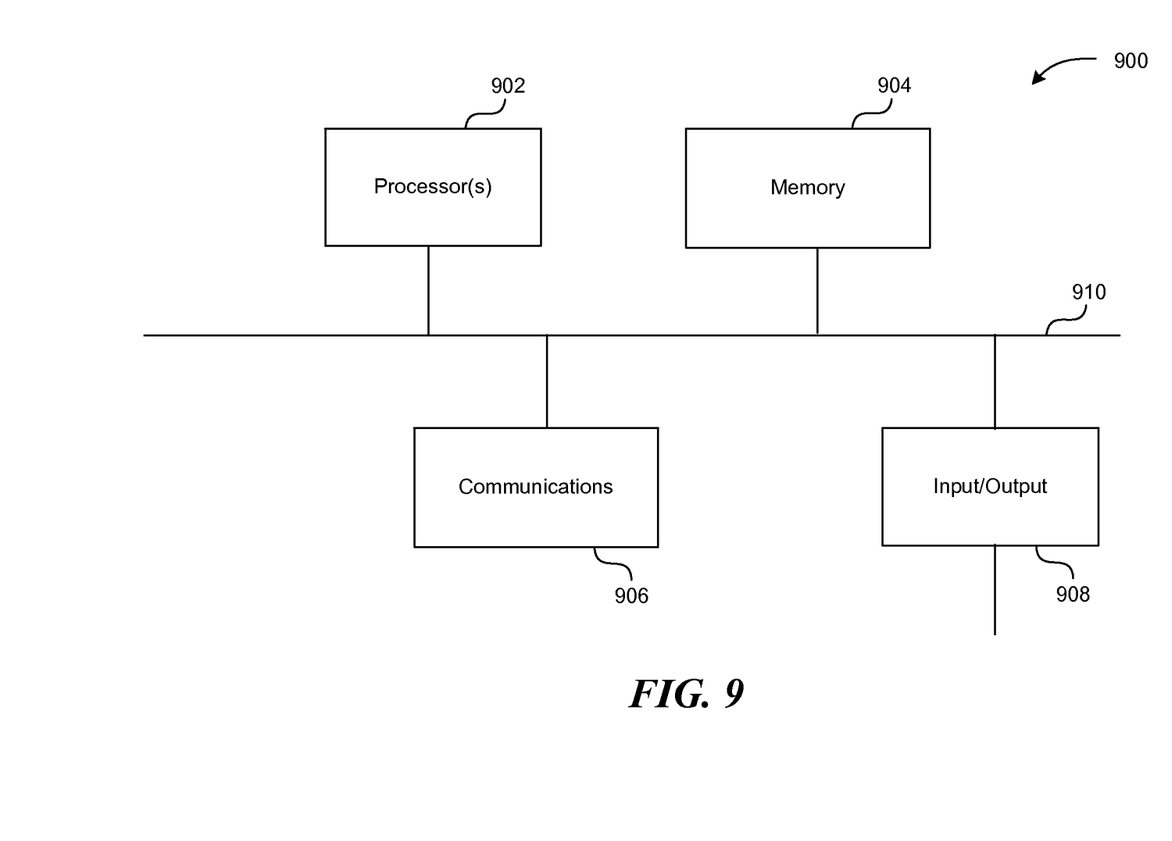
FIG. 9 is a high-level block diagram showing an example architecture of a computer, which may represent any electronic device, any server, or any node within a cloud service as described herein.

FIG. 9 contains a high-level block diagram showing an example architecture of a computer, which may represent any electronic device, such as a mobile device or a server, including any node within a cloud service as described herein, such as may implement the operations described above. The computer 900 includes one or more processors 910 and memory 920 coupled to an interconnect 930. The interconnect 930 shown in FIG. 9 is an abstraction that represents any one or more separate physical buses, point to point connections, or both connected by appropriate bridges, adapters, or controllers. The interconnect 930, therefore, may include, for example, a system bus, a Peripheral Component Interconnect ("PCI") bus or PCI-Express bus, a HyperTransport or industry standard architecture ("ISA") bus, a small computer system interface ("SCSI") bus, a universal serial bus ("USB"), IIC ("I2C") bus, or an Institute of Electrical and Electronics Engineers ("IEEE") standard 1394 bus, also called "Firewire".

The processor(s) 910 is/are the central processing unit ("CPU") of the computer 900 and, thus, control the overall operation of the computer 900. In certain embodiments, the processor(s) 910 accomplish this by executing software or firmware stored in memory 920. The processor(s) 910 may be, or may include, one or more programmable general-purpose or special-purpose microprocessors, digital signal processors ("DSPs"), programmable controllers, application specific integrated circuits ("ASICs"), programmable logic devices ("PLDs"), field-programmable gate arrays ("FPGAs"), trusted platform modules ("TPMs"), or a combination of such or similar devices.

The memory 920 is or includes the main memory of the computer 900. The memory 920 represents any form of random access memory ("RAM"), read-only memory ("ROM"), flash memory, or the like, or a combination of such devices. In use, the memory 920 may contain code 970 containing instructions according to the techniques disclosed herein.

Also connected to the processor(s) 910 through the interconnect 930 are a network adapter 940 and a mass storage device 950. The network adapter 940 provides the computer 900 with the ability to communicate with remote devices over a network and may be, for example, an Ethernet adapter. The network adapter 940 may also provide the computer 900 with the ability to communicate with other computers.

The code 970 stored in memory 920 may be implemented as software and/or firmware to program the processor(s) 910 to carry out actions described above. In certain embodiments, such software or firmware may be initially provided to the computer 900 by downloading it from a remote system through the computer 900 (e.g., via network adapter 940).

CONCLUSION

The techniques introduced herein can be implemented by, for example, programmable circuitry (e.g., one or more microprocessors) programmed with software and/or firmware, or entirely in special-purpose hardwired circuitry, or in a combination of such forms. Software or firmware for use in implementing the techniques introduced here may be stored on a machine-readable storage medium and may be executed by one or more general-purpose or special-purpose programmable microprocessors.

In addition to the above mentioned examples, various other modifications and alterations of the invention may be made without departing from the invention. Accordingly, the above disclosure is not to be considered as limiting, and the appended claims are to be interpreted as encompassing the true spirit and the entire scope of the invention.

The various embodiments are described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

A "machine-readable storage medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible storage medium includes recordable/non-recordable media (e.g., read-only memory (ROM); random access memory (RAM); magnetic disk storage media; optical storage media; flash memory devices; etc.), etc.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatuses, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The aforementioned flowchart and diagrams illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

The invention claimed is:

1. A head-mounted device including sensory stimulation comprising:
    glasses connected to a computer network and a local processor, wherein the glasses are configured to display video data on lenses;
    speakers mounted on the glasses;
    a sensory stimulator mounted on one of a plurality of docking ports on said head-mounted device, said sensory stimulator comprising any of: a nose mask, a facemask, or a lens-mounted device; and
    wherein the sensory stimulator is activated according to instructions received through a first docking port upon satisfaction of a condition, wherein said condition comprises whether said sensory stimulator is mounted on the first docking port, and receipt of an embedded metadata cue associated with video data displayed on the lenses of the glasses, said instruction comprising an action to be performed.

2. The head-mounted device of claim 1, wherein said sensory stimulator comprises a scent dispenser and the action performed is the release of scented material.

3. The head-mounted device of claim 1, wherein said sensory stimulator comprises a taste dispenser and the action performed is the release of flavored material.

4. The head-mounted device of claim 1, wherein said sensory stimulator comprises a water dispenser and the action performed is the release of spray water on a wearer's face.

5. The head-mounted device of claim 1, wherein said action performed is user adjustable in intensity.

6. The head-mounted device of claim 1, further comprising a plurality of instruments including a camera directed at a user eye and a microphone directed at a user mouth.

7. The head-mounted device of claim 6, wherein said plurality of instruments includes an eye pressure sensor configured to measure a user eye pressure, and further configured to send said measurement to an electronic module.

8. The head-mounted device of claim 1, wherein said condition further includes receipt of an external instruction from a device wirelessly communicative with the head mounted device.

9. The head-mounted device of claim 1, wherein said condition further includes receipt of an analysis of video data displayed on the lenses.

10. The head-mounted device of claim 1, wherein said glasses are configured to lengthen or shorten to better fit a user.

11. The head-mounted device of claim 1, wherein the glasses further comprise:
    a second lens, configured to become transparent, semi-transparent, and opaque based on said received instruction.

* * * * *